US010021900B2

(12) United States Patent
Shimada et al.

(10) Patent No.: US 10,021,900 B2
(45) Date of Patent: Jul. 17, 2018

(54) CARBOHYDRATE COMPOSITION AND FOOD AND BEVERAGE PRODUCING GRADUAL RISE IN BLOOD GLUCOSE LEVELS

(71) Applicant: MATSUTANI CHEMICAL INDUSTRY CO., LTD., Itami-shi, Hyogo (JP)

(72) Inventors: Kensaku Shimada, Minoo (JP); Yuko Uehara, Toyonaka (JP)

(73) Assignee: MATSUTANI CHEMICAL INDUSTRY CO., LTD., Itami-shi, Hyogo (JP)

( * ) Notice: Subject to any disclaimer, the term of this patent is extended or adjusted under 35 U.S.C. 154(b) by 0 days.

(21) Appl. No.: 13/653,550

(22) Filed: Oct. 17, 2012

(65) Prior Publication Data

US 2013/0101697 A1 Apr. 25, 2013

(30) Foreign Application Priority Data

Oct. 21, 2011 (JP) .................................. 2011-231317

(51) Int. Cl.
| | |
|---|---|
| *A23L 2/60* | (2006.01) |
| *A23L 21/10* | (2016.01) |
| *A23L 29/30* | (2016.01) |
| *A23L 33/00* | (2016.01) |
| *A23L 33/20* | (2016.01) |

(52) U.S. Cl.
CPC ................ *A23L 2/60* (2013.01); *A23L 21/10* (2016.08); *A23L 29/35* (2016.08); *A23L 33/20* (2016.08); *A23L 33/40* (2016.08)

(58) Field of Classification Search
CPC ...................................................... A23L 1/307
USPC ............................................................. 462/2
See application file for complete search history.

(56) References Cited

U.S. PATENT DOCUMENTS

| | | | |
|---|---|---|---|
| 8,637,487 | B2 | 1/2014 | Van De Heijning et al. |
| 2004/0219141 | A1 | 11/2004 | Kashimura et al. |
| 2008/0193596 | A1 | 8/2008 | Hausmanns et al. |
| 2008/0206311 | A1 | 8/2008 | Kashimura et al. |
| 2010/0069327 | A1 | 3/2010 | Van De Heijning et al. |
| 2011/0008486 | A1 | 1/2011 | Kashimura et al. |
| 2011/0009358 | A1 | 1/2011 | Kashimura et al. |
| 2011/0020496 | A1 | 1/2011 | Shimada et al. |

FOREIGN PATENT DOCUMENTS

| | | |
|---|---|---|
| CN | 1711034 A | 12/2005 |
| CN | 1761406 A | 4/2006 |
| CN | 101252848 A | 8/2008 |
| CN | 101626696 A | 1/2010 |
| CN | 102027022 A | 4/2011 |
| JP | 2007-031445 A | 2/2007 |
| JP | 2007314451 A | 12/2007 |
| WO | 2006104137 A1 | 10/2006 |
| WO | 2009/113652 A1 | 9/2009 |

OTHER PUBLICATIONS

Arai,Effect of a Novel Palatinose-Based Liquid Balanced Formula (MHN-01) on Glucose and Lipid Metabolism in Male Sprague-Dawley Rats After Short- and Long-Term Ingestion, Effect of Palatinose-Based Formula, 2004, 977, 983.*
Japan Patent Office, Office Action dated Aug. 26, 2015 in Japanese Application No. 2011-231317.
J. Kashimura et al., "Inhibitory Action of Palatinose and Its Hydrogenated Derivatives on the Hydrolysis of α-Glucosylsaccharides in the Small Intestine," J. Agric. Food Chem. Jul. 23, 2008:56(14), 5892-5895.
State Intellectual Property Office of People's Republic of China, communication dated Jan. 15, 2015 in corresponding Chinese Application No. 201210399365.7.
Liao et al., "Effect of Isomaltulose on Blood Glucose and Lipids of Diabetic Subjects", Acta Nutrimenta Sinica vol. 23, No. 4, Dec. 31, 2001, p. 373-375.
Miao et al.,"Research Drogress of Low Glycemic-index Starchy Derivatives", Food Science, vol. 29, No. 01, Jan. 31, 2008, p. 452-456.

* cited by examiner

*Primary Examiner* — Michele L Jacobson
*Assistant Examiner* — Philip Dubois
(74) *Attorney, Agent, or Firm* — Sughrue Mion, PLLC

(57) ABSTRACT

Novel findings have been made that a carbohydrate composition in which a highly branched dextrin and isomaltulose are mixed at a specific ratio, wherein the highly branched dextrin has a structure in which glucose or isomaltooligosaccharide is bound to a non-reducing terminus of a dextrin via an α-1,6 glycosidic bond, and has a DE value of 10 to 52, enhances an suppressing effect on digestion of the highly branched dextrin by isomaltulose, that is, synergistically suppresses the digestion, thereby leading to the completion of the present invention.

5 Claims, No Drawings

CARBOHYDRATE COMPOSITION AND FOOD AND BEVERAGE PRODUCING GRADUAL RISE IN BLOOD GLUCOSE LEVELS

TECHNICAL FIELD

The present invention relates to a carbohydrate composition, food and beverage and nutritional supplement product comprising (i) a highly branched dextrin whose DE is 10 to 52 and that has a structure in which glucose or isomaltooligosaccharide is bound to non-reducing termini of starch decomposition products (dextrins) having a branched structure and/or a linear structure within a molecule via an $\alpha$-1,6 glycosidic bond, and (ii) isomaltulose. The composition produces a gradual rise in blood glucose levels.

BACKGROUND ART

Carbohydrates are important nutrients used as our energy source. When taken, the carbohydrates are digested by enzymes in the gastrointestinal tract and absorbed in the small intestine. As a result, blood glucose levels increase. In the case of healthy individuals, when blood glucose levels increase, insulin is secreted from the pancreas to lower blood glucose levels. On the other hand, in the case of diabetic patients, the blood glucose levels continue to stay high because a required amount of insulin is not produced or secreted, or because, even when secreted, insulin has decreased effects. Diabetes mellitus is divided into type I and type II. The former is characterized by insulin not being produced due to genetic causes whereas the latter is characterized by reduced abilities of insulin secretion or decreased effects of insulin due to lifestyle such as obesity, lack of exercise or the like. Among the diabetic patients, 90% or more are those with type II diabetes mellitus. Recently, these patients with type II diabetes mellitus have been rapidly increasing, which becomes serious social concerns. Prevention of diabetes mellitus thus attracts much attention. It is considered that type II diabetes mellitus can be treated or the onset thereof can be prevented mainly by changing one's dietary life for the better.

At present, carbohydrates used commonly in food products such as starch, starch decomposition products or the like are quickly digested and absorbed and, when taken, produce a rapid rise in blood glucose levels. Such materials are unsuitable for diabetic patients and carbohydrates that are more slowly digested and absorbed and produce a gradual rise in blood glucose levels are wanted. (It is prerequisite that their energy coefficient is 4 kcal/kg which is same as that of carbohydrates.) In addition, when used as carbohydrates in nutritional supplement products or the like, glucose or the like has a high osmotic pressure, which induces osmotic diarrhea. Thus, ones with as low an osmotic pressure as possible such as dextrins obtained by hydrolyzing starch with acids or enzymes is wanted. Accordingly, development of carbohydrates that are insusceptible to digestion and have a lower osmotic pressure is extremely helpful for diabetic patients. Further, carbohydrates that are insusceptible to digestion and have a lower osmotic pressure can also be used as a carbohydrate source for diet food products, energy supplement drinks, nutritional supplement food products and the like. Developing those is extremely significant.

As carbohydrates for nutritional supplement products that meet those needs, isomaltulose has been known. Isomaltulose is a disaccharide in which one molecule of glucose and one molecule of fructose are linked via an $\alpha$-1,6 bond and a carbohydrate whose rate of digestion and absorption in the small intestine is slower, and is at present utilized as carbohydrates used in some nutritional supplement products. Yet, an aqueous solution of 10% by mass isomaltulose shows an osmotic pressure of as high as about 340 mOSMOL/kg, which in some cases limits its use.

Moreover, a highly branched dextrin characterized by having a structure in which glucose or isomalto oligosaccharide is bound to a non-reducing terminus of a dextrin via an $\alpha$-1,6 bond and having a DE value of 10 to 52 (hereinafter also referred to simply as highly branched dextrin) has been disclosed (Patent Document 1). This highly branched dextrin exhibits a slower rate of digestion and absorption in the small intestine, and a 10% by mass aqueous solution thereof shows an osmotic pressure of 70 to 300 mOSMOL/kg, which is low. It may thus be used as carbohydrates in nutritional supplement products. Yet, its GI value which was considered as an index for a rise in blood glucose was not necessarily satisfactory.

Furthermore, it has been reported that, when taken concurrently with other carbohydrates such as sucrose, glucose, high-fructose corn syrup, dextrins and/or branched dextrins, isomaltulose exerts an effect of making digestion and absorption of those carbohydrates more gradually and suppressing a rise in blood glucose (Patent Document 2). However, Patent Document 2 shows no examples for actual evaluation of such an effect on blood glucose levels in cases where isomaltulose is used in combination with dextrins or branched dextrins, and it merely discloses examples with sucrose or glucose being used.

PRIOR ART REFERENCES

Patent Documents

[Patent Document 1] WO 2009/113652
[Patent Document 2] Japanese Patent Application Laid-Open Publication No. 2007-31445

SUMMARY OF THE INVENTION

Problems to be Solved by the Invention

In light of such circumstances, the present invention has been made. An object thereof is to provide a carbohydrate composition and a food and beverage that is, when taken, slowly digested and absorbed in the small intestine, produces a gradual rise in blood glucose levels, as well as has as low an osmotic pressure as possible.

Means for Solving the Problems

The present inventors intensively studied on carbohydrates that are insusceptible to digestion, produce a gradual rise in blood glucose levels, and have as low an osmotic pressure as possible; and, as a result, found a novel finding that a carbohydrate composition in which a highly branched dextrin and isomaltulose are mixed at a specific ratio, wherein the highly branched dextrin has a structure in which glucose or isomaltooligosaccharide is bound to a non-reducing terminus of a starch decomposition product (dextrin) having a branched structure and/or a linear structure within a molecule via an $\alpha$-1,6 glycosidic bond, and has a DE value of 10 to 52, enhances the suppressing effect of isomaltulose on digestion of the highly branched dextrin, that is, synergistically suppresses the digestion, thereby completing the present invention. Accordingly, the present invention provides the following.

1. A carbohydrate composition comprising (i) a highly branched dextrin whose DE is 10 to 52 and that has a structure in which glucose or isomaltooligosaccharide is bound to a non-reducing terminus of the dextrin via an α-1,6 glycosidic bond, and (ii) isomaltulose.

2. The carbohydrate composition according to the above-mentioned 1, wherein a weight ratio between the highly branched dextrin and the isomaltulose ranges from 1:0.6 to 1:2.

3. The carbohydrate composition according to the above-mentioned 1 or 2, wherein a ratio of glucose bound to the non-reducing terminus of glucose or isomaltooligosaccharide via α-1,6 glycosidic bond is not less than 5% by mass based on the total mass of the highly branched dextrin.

4. The carbohydrate composition according to any one of the above-mentioned 1 to 3, wherein a ratio of glucose having an internally branched structure is 4 to 13% by mass based on the total mass of the highly branched dextrin.

5. A food and beverage comprising the carbohydrate composition according to any one of the above-mentioned 1 to 4.

6. The food and beverage according to the above-mentioned 5 which is a nutritional supplement, a fluid diet, a meal substitute beverage, an energy supplement drink, or a jelly food.

7. A method for inhibiting digestion of highly branched dextrin in a human or in an animal, comprising a step of administering the carbohydrate composition of claim 1 to the human or the animal.

8. The method according to the above-mentioned 7, wherein the slow digestion of highly branched dextrin is achieved by an inhibitory action on the digestion of highly branched dextrin by the isomaltulose in the composition of the above-mentioned 1.

9. The method according to the above-mentioned 7, wherein a weight ratio between the highly branched dextrin and isomaltulose ranges from 1:0.6 to 1:2.

10. The method according to the above-mentioned 7, wherein a ratio of glucose bound to said non-reducing terminus of glucose or isomaltooligosaccharide via α-1,6 glycosidic bond is not less than 5% by mass based on the total mass of said highly branched dextrin.

11. The method according to the above-mentioned 7, wherein a ratio of glucose having an internally branched structure is 4 to 13% by mass based on the total mass of said highly branched dextrin.

Effect of the Invention

Because a composition obtained by the present invention is, when taken, slowly digested and absorbed in the small intestine, produces an effectively suppressed rise in blood glucose levels and has a lower osmotic pressure, it can be expected that the composition is applied to the field of a wide range of medical diet products and food products, by being used as a carbohydrate source of nutritional supplement products for diabetic patients, diet food products, energy supplement drinks, and nutritional supplement food products.

MODE FOR CARRYING OUT THE INVENTION

The term DE, when used in the present invention, refers to a value represented by an equation of "{(mass of direct reducing sugar (indicated as glucose))/(mass of solid content)}×100" and an analysis value by the Willstatter and Schudel method.

The term "highly branched dextrin", when used in the present invention, refers to a dextrin having a structure in which glucose or isomaltooligosaccharide is bound to the non-reducing terminus of the dextrin via an α-1,6 glycosidic bond and having a DE of 10 to 52.

DE is preferably 15 to 30 and further preferably 15 to 25.

The osmotic pressure of a carbohydrate composition of the present invention is preferably approximately 70 to 300 mOSMOL/kg, and more preferably 100 to 200 mOSMOL/kg. The term osmotic pressure, when used in the present invention, refers to a value obtained by measuring an aqueous solution adjusted in 10% Brix by a freezing point depression method using an osmometer (VOGEL OM802-D).

For details, a percentage of glucose whose non-reducing terminus is bound to glucose or isomaltooligosaccharide via an α-1,6 glycosidic bond, that is, a percentage of "→6)-Glcp-(1→" is preferably not less than 5% by mass based on the entire mass of dextrins, further preferably not less than 7% by mass, and particularly preferably 8 to 30% by mass. Further, a percentage of glucose having an internally branched structure, that is, a percentage of "→4,6)-Glcp-(1→" is preferably 4 to 13% by mass based on the entire mass of dextrins, and further preferably 5 to 10% by mass.

A percentage of these bonds can be confirmed by a method by Ciucanu et al., which method is modified from a methylation method by Hakomori (Carbohydr. Res., 1984, 131, 209-217).

As for the highly branched dextrin used in the present invention that has a structure in which glucose or isomaltooligosaccharide is bound to a non-reducing terminus of a starch decomposition product (dextrin) having a branched structure and/or a linear structure within a molecule via an α-1,6 glycosidic bond, and has a DE value of 10 to 52, one which is commercially available can be used. It is, for example, sold under a trade name of "HBD-20" from Matsutani Chemical Industry Co., Ltd.

As for isomaltulose used in the present invention, one which is commercially available can be utilized. It is, for example, is sold under a trade name of "Palatinose(R)" from Mitsui Sugar Co., Ltd.

A carbohydrate composition of the present invention can be prepared by combining the above-mentioned highly branched dextrin and isomaltulose. As for a combination ratio, for 1 part by mass of highly branched dextrins, 0.6 to 2.0 parts by mass of isomaltulose, preferably 0.8 to 2.0 parts by mass, further preferably 1.0 to 2.0 parts by mass. In cases where isomaltulose is below 0.6 parts by mass, a digestion suppressing effect is weak, whereas in cases where it is above 2.0 parts by mass, the digestion suppressing effect is strong but osmotic pressure is high, which limits its use in nutritional supplement products or the like.

This composition may be a simple mixture of powders but can take various dosage forms depending on applications such as granules, tablets, paste, solution or the like.

Further, this composition is expected to be used mainly in nutritional supplement products for medical diets, food products for nursing care, meal substitute foods and beverages, diet food products, foods and beverages for sports and the like, but can be used in almost all of the food products. This food product refers to a general term of food products for human, baits and animal feeds in zoo, pet foods, and the like; and all of the food products in which conventional starch decomposition products whose DE is approximately 20 to 48 can be used are included. That is, it can be effectively used in liquid and powdered beverages such as coffee, tea, cola, juice or the like; bakeries such as bread, cookies, biscuits, cakes, pizzas, pies, or the like; noodles such as Japanese wheat noodles, ramen noodles, Japanese buckwheat noodles or soba, or the like; pasta such as spaghetti, macaroni, fettuccine, or the like; confectionary/confectionery such as candies, chocolates, chewing gums, or the like; fried snack foods such as doughnuts, potato chips, or the like; ice cream such as ice cream, shake, sherbet, or the like; dairy products such as cream, cheese, powdered milk, condensed milk, creamy powder, coffee whitener, milk beverage or the like; chilled desserts such as puddings, yogurts, yogurt drinks, jellies, mousse, Bavarian cream or bavarois, or the like; retort pouch or canned foods such as various soup, stew, gratin, curry, or the like; seasonings and condiments such as various fermented soybean paste or miso, soy sauce, sauce, ketchup, mayonnaise, dressing, bouillon, various roux, or the like; processed meat products and frozen food products thereof such as ham, sausage, patty or Salisbury steak, meatball, corned beef, or the like; frozen processed food products such as pilaff, croquette, omelette, rice casserole with white sauce or doria, or the like; processed marine products such as crab stick, steamed fish paste or kamaboko, or the like; processed agricultural products such as dry mashed potato, jam, marmalade, peanut butter, peanut, or the like; and others including foods boiled down in soy or tsukudani, rice cakes, rice confectionery, snack food products, and fast foods.

A composition of the present invention can be used in an unchanged form as the above energy supplements. Preferably, it is appropriate for the composition to be contained in nutritional supplement products for medical diets, food products for nursing care, meal substitute foods and beverages, diet food products, foods and beverages for sports and the like in an amount of 3 to 50% by mass, and preferably approximately 10 to 30% by mass. A method of combination includes a method in which all or part of starch or carbohydrates in a food product are substituted with a composition of the present invention, a method in which a composition of the present invention is newly added to be combined, and the like, but is not limited thereto.

Moreover, when the composition of the present invention is used in nutritional supplements for medical diets, food products for nursing care, meal substitute foods and beverages, diet food products, foods and beverages for sports and the like, combined use with other functional food product materials, such as indigestible dextrins or the like is expected to further enhance its effect.

EXAMPLES (Experimental Example 1) (In Vitro Digestibility Test)

By way of examples, the present invention will be concretely described below. But the present invention is by no means limited thereto. Unless otherwise noted, % represents % by mass An inhibitory effect of isomaltulose on in vitro digestion of a highly branched dextrin and standard dextrin was examined by an in vitro digestibility test.

The in vitro digestibility test in the present invention is a mock test for carbohydrate digestibility within a living organism, and a test by a modified method on the basis of a method of Englyst et al. (European Journal of Clinical Nutrition, 1992, 46 S33-S50), wherein carbohydrates (dextrins in the case of the present invention) is broken down by an enzyme mix solution (swine pancreatic amylase and rat small intestine mucosa enzyme) to release glucose and the amount of the resulting glucose is measured with time.

Swine pancreatic amylase used was one manufactured by Roche (19230 U/ml). The rat small intestine mucosa enzyme was prepared from rat small intestinal acetone powders manufactured by Sigma and used. More specifically, 1.2 g of rat small intestinal acetone powders was suspended in 15 ml of 45 mM Bis-Tri.s.Cl buffer (pH6.6)/0.9 mM $CaCl_2$. The suspension was homogenized and then centrifuged at 3000 rpm for 10 minutes. The obtained supernatant was used as a crude enzyme solution of rat small intestine mucosa enzyme. The activity of the crude enzyme solution was calculated by taking an activity to break down 1 mmol of maltose in a 26 mM maltose solution for one minute as 1 U.

The test method is as follows.

With regard to test substances, a highly branched dextrin having a structure in which glucose or isomaltooligosaccharide is bound to a non-reducing terminus of a dextrin via an $\alpha$-1,6 glycosidic bond, and having a DE of 10 to 52 (trade name HBD-20: manufactured by Matsutani Chemical Industry Co., Ltd./DE=20) (a percentage of glucose whose non-reducing terminus is bound to glucose or isomaltooligosaccharide via an $\alpha$-1,6 glycosidic bond: 8.9%; a percentage of glucose having an internally branched structure: 5.2%) and, as a control, standard dextrin (trade name TK-16: manufactured by Matsutani Chemical Industry Co., Ltd./DE=18) (a percentage of glucose whose non-reducing terminus is bound to glucose or isomaltooligosaccharide via an $\alpha$-1,6 glycosidic bond: 0.0%; a percentage of glucose having an internally branched structure: 4.8%) were used. Each of them was dissolved in pure water to prepare a 2% by mass solution. In addition, isomaltulose (trade name Palatinose (R): manufactured by Mitsui Sugar Co., Ltd.) was used as an inhibitor.

For each of the test substances, one tube for a system with isomaltulose not being added (test substance alone) and five tubes for a system with isomaltulose being added (test substance+Palatinose(R)) were provided and reaction solutions were prepared.

In the system with isomaltulose not being added (test substance alone), 150 µl of solution of 2% by mass test substance and 1270 µl of buffer solution (45 mM Bis-Tris.Cl Buffer (pH6.6)/0.9 mM $CaCl_2$) were added and stirred well.

Meanwhile, in the system with isomaltulose being added (test substance+Palatinose(R)), 150 µl of solution of 2% by mass test substance was added to each of 75, 90, 120, 150, and 300 µl of solution of 2% by mass isomaltulose, and then a buffer solution was added such that the entire amount is 1420 µl. The resultant was stirred well. In the system with isomaltulose being added (test substance+Palatinose(R)), the amount of isomaltulose was added so as to be 0.5 times, 0.6 times, 0.8 times, one time, twice as much as the amount of test substance, respectively.

An enzyme mix solution was prepared by mixing 8 µl of swine pancreatic amylase (384.6 U/ml), 22.4 µl of rat small intestine mucosa enzyme (6.33 U/ml), and 49.6 µl of buffer solution, so that 80 µl of the solution is added to one reaction solution. The prepared reaction solution was subjected to preliminary incubation at 37° C. for 10 minutes. Subsequently, 25 µl of 0.5 M perchloric acid was mixed well with 95 µl of reaction solution and 5 µl of enzyme mix solution, and the resultant was used as a sample at reaction time 0 minutes.

Next, the remaining reaction solution was added with 75 µl of enzyme mix solution and mixed well to begin a reaction at 37° C. At reaction time 10 minutes, 30 minutes, and 3 hours, 100 μl of reaction solution was taken and mixed with 25 μl of 0.5

M perchloric acid to terminate the reaction. 40 μl of this solution in which the reaction had been terminated was subjected to Glucose CII Test Wako (manufactured by Wako Pure Chemical Industries, Ltd.) to quantify glucose concentration at each reaction time. A percentage of decrease in the rate of glucose production when isomaltulose was added was calculated from the quantified glucose concentration by the following calculation method and used as an index of the inhibitory effect.

The rate of glucose production per hour from reaction time 0 minutes to each reaction time is calculated from glucose concentration (reaction time 0 minutes: A mg/dl, each reaction time: B mg/dl) in a system with isomaltulose not being added.

Rate of glucose production (mg/dl/h)=$(B-A)$/Reaction time (h)    X

Likewise, the rate of glucose production per hour from reaction time 0 minutes to each reaction time is calculated from glucose concentration (reaction time 0 minutes: C mg/dl, each reaction time: D mg/dl) in a system with isomaltulose being added.

Rate of glucose production (mg/dl/h)=$(D-C)$/Reaction time (h)    Y

From the rate of glucose production in the system with isomaltulose not being added and the system with isomaltulose being added (X, Y), a percentage of decrease in the rate of glucose production when isomaltulose was added was determined for each reaction time, as compared with that in a system with isomaltulose being added.

Percentage of decrease in rate of glucose production (%)=$(X-Y)$/X×100

For each of the amount of isomaltulose (Palatinose(R)) added, the rate of glucose production and percentage of decrease are individually shown in Table 1. Experiment 1 showed effects when 0.5, 1.0 and 2.0 parts by mass of isomaltulose was added for 1 part by mass of test substance whereas Experiment 2 showed effects when 0.6 and 0.8 parts by mass of isomaltulose was added.

When 0.6 parts by mass or more of isomaltulose were added for 1 part by mass of test substance, as compared with the standard dextrin (TK-16), a percentage of decrease in the rate of glucose production in the highly branched dextrin (HBD-20) was higher, which indicated a higher inhibitory effect against a breakdown reaction of the highly branched dextrin, that is, a synergistic inhibitory effect.

Furthermore, when 0.6 parts by mass or more of isomaltulose were added for 1 part by mass of test substance, as the amount of isomaltulose added increased a difference between a percentage of decrease in the rate of glucose production in the standard dextrin and the highly branched dextrin became more significant. Thus, the synergistic inhibitory effect of isomaltulose on the breakdown of highly branched dextrin was established (confirmed).

TABLE 1

Effect of Isomaltulose on In Vitro Digestibility of Dextrin or Highly Branched Dextrin

| | Amount of Palatinose(R) added | Reaction time (minutes) | Rate of glucose production [1] (Percentage of decrease in the rate [2]) | |
|---|---|---|---|---|
| | | | TK-16 | HBD-20 |
| Experiment 1 | 0 | 10 | 62.1 (—) | 50.9 (—) |
| | | 30 | 46.6 (—) | 38.2 (—) |
| | | 180 | 29.8 (—) | 20.9 (—) |
| | 0.5 | 10 | 61.4 (1.1) | 50.8 (0.2) |
| | | 30 | 46.7 (−0.2) | 36.7 (3.8) |
| | | 180 | 29.4 (1.4) | 20.7 (1.1) |
| | 1.0 | 10 | 60.9 (1.9) | 45.7 (10.2) |
| | | 30 | 46.2 (0.9) | 34.3 (10.2) |
| | | 180 | 29.1 (2.3) | 19.9 (4.7) |
| | 2.0 | 10 | 60.3 (2.9) | 43.5 (14.4) |
| | | 30 | 44.9 (3.7) | 33.0 (13.7) |
| | | 180 | 28.4 (4.8) | 18.6 (11.0) |
| Experiment 2 | 0 | 10 | 59.1 (—) | 48.7 (—) |
| | | 30 | 44.6 (—) | 35.1 (—) |
| | | 180 | 28.6 (—) | 20.0 (—) |
| | 0.6 | 10 | 58.5 (1.1) | 47.0 (3.5) |
| | | 30 | 43.4 (2.7) | 34.1 (3.0) |
| | | 180 | 28.7 (−0.3) | 19.4 (3.2) |
| | 0.8 | 10 | 58.5 (1.1) | 47.5 (2.4) |
| | | 30 | 43.4 (2.8) | 33.8 (3.9) |
| | | 180 | 28.4 (0.8) | 19.2 (4.1) |

[1] mg/dl/h
[2] %

Example 1

Preparation of Enteral Nutritional Supplement

An enteral nutritional supplement containing HBD-20 (osmotic pressure: 140 mOSM) and Palatinose(R) which were checked in Experimental Example 1 was prepared in accordance with the formulation of Table 2 and an excellent product was obtained.

TABLE 2

| Name of raw material | Formulation (parts by mass) |
|---|---|
| HBD-20 | 5.00 |
| Palatinose(R) | 5.00 |
| Sugar | 5.00 |
| Casein sodium | 2.00 |
| Milk protein | 1.50 |
| Corn oil | 1.50 |
| Safflower oil | 1.50 |
| Neutral fat acid triglyceride | 0.50 |
| Sodium citrate | 0.25 |
| Flavoring agents | 0.20 |
| Milk whey minerals | 0.20 |
| Potassium chloride | 0.15 |
| Magnesium chloride | 0.15 |
| Egg white | 0.10 |
| Soybean peptide | 0.10 |
| Lecithin | 0.05 |
| Vitamin C | 0.006 |
| Methionine | 0.005 |
| Vitamin E | 0.005 |
| Ferric sodium citrate | 0.0075 |
| Niacin | 0.0013 |
| Calcium pantothenate | 0.0006 |
| Vitamin B6 | 0.00013 |
| Vitamin B2 | 0.00011 |
| Vitamin B1 | 0.00008 |
| Vitamin A | 250 (IU) |

TABLE 2-continued

| Name of raw material | Formulation (parts by mass) |
|---|---|
| Leaf acid | 0.000015 |
| Vitamin D | 12 (IU) |
| Vitamin B12 | 0.00000012 |
| Water | Added to obtain an equivalent to 100 parts by mass |

Example 2

Preparation of Meal Substitute Beverage

A beverage for meal substitute containing HBD-20 (osmotic pressure: 140 mOSM) and Palatinose(R) which were checked in Experimental Example 1 was prepared in accordance with the formulation of Table 3 and an excellent product was obtained.

TABLE 3

| Name of raw material | Formulation (parts by mass) |
|---|---|
| HBD-20 | 5.00 |
| Palatinose(R) | 5.00 |
| Sugar | 5.0 |
| Milk protein | 5.0 |
| Rice oil *1 | 1.0 |
| Cocoa powder | 1.0 |
| Microcrystalline cellulose *2 | 0.5 |
| Emulsifier *3 | 0.05 |
| Potassium chloride | 0.1 |
| Vitamin mix *4 | 0.1 |
| Flavor *5 | 0.1 |
| Water | Added to obtain an equivalent to 100 parts by mass |

*1 manufactured by Tsuno Food Industrial Co.
*2 manufactured by Asahi Kasei Corporation (Avicel CL-611S)
*3 manufactured by Mitsubishi Kagaku Foods Corporation (sugar ester P-1670)
*4 manufactured by Takeda Pharmaceutical Co., Ltd. (New ViRich WS-7L)
*5 manufactured by Takata Koryo Co., Ltd. (custard vanilla essenceT-484)

Example 3

Preparation of Energy Supplement Drink

An energy supplement drink containing HBD-20 (osmotic pressure: 140 mOSM) and Palatinose(R) which were checked in Experimental Example 1 was prepared in accordance with the formulation of Table 4 and an excellent product was obtained.

TABLE 4

| Name of raw material | Formulation (parts by mass) |
|---|---|
| HBD-20 | 10.00 |
| Palatinose(R) | 10.00 |
| Fructose | 3.0 |
| Citric acid | 0.13 |
| Sodium citrate | 0.05 |
| Vitamin C | 0.05 |
| Caffeine | 0.01 |
| Sodium chloride | 0.01 |
| Potassium chloride | 0.01 |
| Flavor * | 0.11 |

TABLE 4-continued

| Name of raw material | Formulation (parts by mass) |
|---|---|
| Water | Added to obtain an equivalent to 100 parts by mass |

* manufactured by Takata Koryo Co., Ltd. (grapefruit essence #2261)

Example 4

Preparation of Jelly

Jelly containing HBD-20 (osmotic pressure: 140 mOSM) and Palatinose(R) which were checked in Experimental Example 1 was prepared in accordance with the formulation of Table 5 and an excellent product was obtained.

TABLE 5

| Name of raw material | Formulation (parts by mass) |
|---|---|
| HBD-20 | 11.00 |
| Palatinose(R) | 11.00 |
| Fructose | 3.0 |
| Polysaccharide thickener *1 | 0.16 |
| Vitamin C | 0.1 |
| Citric acid | 0.08 |
| Calcium lactate | 0.06 |
| Sodium chloride | 0.03 |
| Potassium chloride | 0.02 |
| Monosodium glutamate | 0.005 |
| ⅕ White grape fruit juice *2 | 0.3 |
| Flavor *3 | 0.1 |
| Water | Added to obtain an equivalent to 100 parts by mass |

*1 manufactured by Dainippon Sumitomo Pharma Co., Ltd. (Kel co-gel)
*2 manufactured by Oyama Company Limited
*3 manufactured by Takata Koryo Co., Ltd. (muscat grape essence #50631)

What is claimed is:

1. A carbohydrate composition comprising (i) a highly branched dextrin whose DE is 10 to 52 and that has a structure in which glucose or isomaltooligosaccharide is bound to a non-reducing terminus of the dextrin via an α-1,6 glycosidic bond, and (ii) isomaltulose,
   wherein a weight ratio between said highly branched dextrin and said isomaltulose ranges from 1:1 to 1:2,
   a ratio of glucose bound to said non-reducing terminus of glucose or isomaltooligosaccharide via an α-1,6 glycosidic bond is not less than 7% by mass based on the total mass of said highly branched dextrin, and
   a ratio of glucose having an internally branched structure is 4 to 13% by mass based on the total mass of said highly branched dextrin.

2. A food and beverage comprising said carbohydrate composition according to claim 1.

3. The food and beverage according to claim 2 which is a nutritional supplement, a fluid diet, a meal substitute beverage, an energy supplement drink, or a jelly food.

4. The carbohydrate composition according to claim 1, wherein the highly branched dextrin (i) is a dextrin with a DE of 20 and a percentage of glucose whose non-reducing terminus is bound to a glucose or isomaltooligosaccharide via an α-1,6-glycosidic bond of 8.9% and a percentage of glucose having an internally branched structure of 5.2%.

5. The carbohydrate composition according to claim 1, wherein the digestion of highly branched dextrin is suppressed by isomaltulose.

* * * * *